United States Patent [19]

Lamberti et al.

[11] 4,405,526

[45] Sep. 20, 1983

[54] PROCESS FOR PRODUCING DIRECTLY ESTERIFIED FATTY ACYL ISETHIONATE BY A MIXED ZINC OXIDE-SULFONIC ACID CATALYST

[75] Inventors: Vincent Lamberti, Upper Saddle River; Laurence K. Boen, Park Ridge, both of N.J.

[73] Assignee: Lever Brothers Company, New York, N.Y.

[21] Appl. No.: 295,943

[22] Filed: Aug. 24, 1981

[51] Int. Cl.$^3$ .................. C07C 143/90; C11D 1/28
[52] U.S. Cl. ................................................ 260/400
[58] Field of Search ........................................ 260/400

[56] References Cited

U.S. PATENT DOCUMENTS

| | | | |
|---|---|---|---|
| 3,004,049 | 10/1961 | Schenck | 260/400 |
| 3,320,292 | 5/1967 | Cahn et al. | 260/400 |
| 3,383,396 | 5/1968 | Cahn et al. | 260/400 |
| 3,394,155 | 7/1968 | Cahn et al. | 260/400 |
| 3,429,136 | 2/1969 | Holt et al. | 260/400 |
| 3,880,897 | 4/1975 | Landy | 260/400 |

FOREIGN PATENT DOCUMENTS

| | | | |
|---|---|---|---|
| 811699 | 4/1959 | United Kingdom | 260/400 |
| 824447 | 12/1959 | United Kingdom | 260/400 |

OTHER PUBLICATIONS

J.A.O.C.S. 44, 157-158 (1967) "A Reference Standard for Quaternary Solutions Used for Titrating Anionic Detergents".
Ann. 605, 111-117 (1957) by Langenbeck et al., "Hydrolytic Effects of Metal Salts of Organic Acids I".
ASTM Standards, Part 10, 1961, pp. 1099-1101.

*Primary Examiner*—Helen M. S. Sneed
*Attorney, Agent, or Firm*—James J. Farrell; Amirali Y. Haidri

[57] ABSTRACT

This invention discloses a method of producing directly esterified fatty acyl isethionate having a yellowness index less than about 6.0, which consists essentially of reacting a fatty acid with an alkali metal isethionate in the presence of a catalyst comprising a mixture of ZnO and an organic sulfonic acid wherein the molar ratio of ZnO to organic solfonic acid is about 1:1.7 or less and heating at about 200° C. to about 255° C. for sufficient time to produce the desired directly esterified fatty acyl isethionate.

5 Claims, No Drawings

PROCESS FOR PRODUCING DIRECTLY ESTERIFIED FATTY ACYL ISETHIONATE BY A MIXED ZINC OXIDE-SULFONIC ACID CATALYST

This invention relates to a zinc catalyzed process for the preparation of directly esterified fatty acyl isethionates (DEFI).

The use of zinc oxide or salts of organic and inorganic sulfonic acids as esterification catalysts is known (see U.S. Pat. No. 3,320,292 and Lagenbeck et al, Ann. 605, 111–17(1957). However, problems, particularly of relatively low reaction rates and/or undesirable dark color formation and/or undesirable corrosivity toward stainless steel are encountered when certain catalysts are utilized employing prior art methods in the esterification of an alcohol of the formula $HOR'SO_3M$ with an organic acid of the formula $RCOOH$ in the preparation of a surface active agent of the formula $RCOOR'SO_3M$, where R is a monovalent aliphatic hydrocarbon radical having from 7 to 19 carbon atoms, R' is selected from the group consisting of divalent aliphatic hydrocarbon radicals containing 2 to 4 carbon atoms and M is an alkali metal cation, particularly sodium, potassium and lithium.

Surface active agents are one of the basic raw materials in the detergent industry. Specifications for such materials generally require the absence of colored impurities in order to prepare high quality, aesthetically pleasant, formulated products such as detergent bars. The absence of colored impurities also minimizes the chance of imparting off-odors to the formulated products.

Hence, a process for the preparation of surface active agents utilizing catalytic systems which provide a relatively light colored DEFI product together with a higher reaction rate and negligible corrosion effects thereby significantly reducing the cost of production, is highly desirable.

It is, therefore, an object of the present invention to substantially overcome the limitations and disadvantages of the prior art methods.

It is another object of the present invention to provide new, zinc-containing catalytic systems for the production of a light colored directly esterified fatty acyl isethionate.

Other objects and advantages will appear as the description proceeds.

The attainment of the above objects is made possible by this invention which includes producing directly esterified fatty acyl isethionate consisting essentially of reacting a fatty acid with an alkali metal isethionate in the presence of a catalyst comprising a mixture of ZnO and an organic sulfonic acid wherein the molar ratio of ZnO to organic sulfonic acid is about 1:1.7 or less and heating at about 200° C. to about 255° C. for sufficient time to produce the desired directly esterified fatty acyl isethionate.

A non-limiting list of suitable organic sulfonic acids is as follows: isethionic acid; methane sulfonic acid; p-toluene sulfonic acid; linear $C_{10-15}$ alkyl benzene sulfonic acids; $C_{14-16}$ α-olefin sulfonic acids; $C_{10-14}$ alkane-1-sulfonic acids; $C_{13-17}$ random paraffin sulfonic acids and the like.

The efficacy of the new catalytic systems was determined by comparing their catalytic activity with the standard ZnO system commercially used in the manufacture of DEFI fully described in the U.S. Pat. No. 3,320,292 and incorporated herein by reference. The reaction conditions employed in the tests described herein are based essentially on the commercial process except that the stearic acid addition and stripping steps are omitted to simplify the determination of the conversion of sodium isethionate into sodium fatty acyl isethionate.

The color of the DEFI products is evaluated by a yellowness index which is measured as follows. A 2.50 g sample of the DEFI product is dissolved in 50 ml of a solvent mixture prepared by mixing (volume basis) 30 parts of isopropanol with 4 parts of concentrated hydrochloric acid and 66 parts of distilled water. Using 10 cm cells, the percent transmission of the freshly prepared solution is read with a spectrophotometer at 550 nm, 430 nm and 400 nm against the solvent in the reference cell. The yellowness index is then calculated from the expression:

$$\text{Yellowness Index} = 2(T_{550}) - (T_{430} + T_{400})$$

where T is the percent transmission at the indicated wavelength.

The following examples without limiting the scope thereof more fully illustrate the embodiments of this invention. All parts and proportions referred to herein and in the appended claims are by weight unless otherwise indicated.

EXAMPLE 1

The teachings of U.S. Pat. No. 3,320,292 were utilized in the process described below. A 100 ml two-piece four-neck glass reactor was fitted with a thermometer, a mechanical stirrer, a nitrogen gas inlet tube, a mechanical (syringe) pump and a condenser. The reactor was charged with 42.9 g (0.207 mole) coconut fatty acid and 0.071 g zinc oxide. The reactor was then heated to about 175° C. using an oil bath. Nitrogen sparging at the rate of 40 cc/minute was started and 21.9 g (0.148 mole) sodium isethionate was added as a 55% solution in water incrementally at the same time. The rate of addition was adjusted so that the temperature remained greater than about 150° C. After the addition of sodium isethionate, the reaction mixture was heated to 221°–238° C., most of the time at 235°–238° C., for 90 minutes during which the nitrogen rate was kept at 80 cc/min.

The water-fatty acid condensate was collected from which the fatty acid was recovered. The DEFI product was allowed to cool under nitrogen and the weight determined. The content of DEFI active, i.e., $RCOOCH_2CH_2SO_3Na$, was then determined by Hyamine (methylene blue) titration [described in ASTM Standards, Part 10, 1961, pp 1099–1101 and J.A.O.C.S. 44, 157 (1967)]. The titration value was corrected for any titratable catalyst present. The percent conversion of sodium isethionate into DEFI active was then readily calculated from the weight of DEFI product obtained, the % DEFI active determined and the theoretical yield of DEFI active based on the weight of the sodium isethionate reactant. The yellowness index was measured according to the formula described previously herein.

In order to test the efficacy of the new catalytic systems, ZnO was replaced either by a pre-prepared zinc salt of an organic sulfonic acid or in situ prepared catalyst by using a mixture of ZnO and an organic sulfonic acid in varying molar ratios. An example of pre-prepared catalyst is Zn(LAS$^-$)$_2$, wherein LAS$^-$ is a linear C$_{10-15}$ alkylbenzene sulfonate anion having its phenyl group randomly attached to the secondary positions along the linear alkyl chains. The sodium salt of the linear alkylbenzene sulfonic acid, also known simply as LAS, is widely used as an anionic surfactant. Zn(LAS$^-$)$_2$ may be prepared as follows: Ten grams of commercial linear C$_{10}$-C$_{15}$ alkylbenzene sulfonic acids containing a total acidity of 4.10 meq. per gram (determined by titration with standard alkali) was dissolved in water. Zinc acetate dihydrate, 4.5 g (2.05 millimoles) was then added and the mixture heated on the steam bath until all solids dissolved. The solution was then freeze-dried in vacuo to recover the residue of Zn(LAS$^-$)$_2$. The zinc salts of other organic sulfonic acids, e.g. methane sulfonic acid, p-toluene sulfonic acid, α-olefin sulfonic acids and isethionic acid may be prepared in a similar manner. Some of the organic sulfonic acids were prepared from commercial preparations of the corresponding sodium salts by passing an aqueous solution of the material through a column of a cation exchange resin to produce the free acid. The levels of catalyst utilized in Table 1 are equivalent in zinc content to the control level, i.e., 0.11% ZnO, basis total weight of fatty acid and sodium isethionate reactants used. In general, about 0.05% to about 5% (calculated as ZnO) of the catalysts may be employed.

The effect of various modes of addition of the catalysts to the reaction mixture were also tested. In the standard mode (A), the catalyst is mixed with the fatty acid charge according to the commercial process referred to above. In reaction mode (B), the catalyst is premixed with the aqueous solution of sodium isethionate and then this premix is added to the fatty acid charge incrementally at 150°-175° C. to remove water followed by heating at 235°-238° C. In reaction mode (C) the catalyst is premixed with the aqueous solution of sodium isethionate and the premix is then added all at once to the fatty acid charge at the room temperature prior to commencing the esterification reaction. The results of these tests are set forth in Table 1.

TABLE 1

THE EFFECT OF NEW CATALYTIC SYSTEMS, DIFFERENT MOLAR RATIOS AND MODE OF ADDITION ON THE COCONUT DEFI CONVERSION AND COLOR

| Catalyst | % DEFI Conversion | | | Color (Yellowness Index) | | |
|---|---|---|---|---|---|---|
| | Mode A | Mode B | Mode C | Mode A | Mode B | Mode C |
| 1. Control (ZnO) | 86.9 | 87.7 | 87.1 | 8.0 | 4.0 | 1.0 |
| 2. Zn(LAS$^-$)$_2$ | 92.3 | 93.0 | 93.9 | 22.0 | 4.0 | 2.0 |
| 3. ZnO/LAS acid = 1:0.5 | 88.8 | 88.9 | — | 8.5 | 5.5 | — |
| 4. ZnO/LAS acid = 1:0.9 | 90.0 | 90.2 | — | 13.0 | 3.5 | — |
| 5. ZnO/LAS acid = 1:1.3 | 90.2 | 91.0 | 90.4 | 17.5 | 3.5 | 1.5 |
| 6. ZnO/LAS acid = 1:1.5 | 91.4 | 92.0 | — | 21.0 | 3.5 | — |
| 7. ZnO/LAS acid = 1:1.7 | 91.9 | 91.7 | 92.2 | 23.0 | 5.5 | 1.5 |
| 8. ZnO/LAS acid = 1:1.9 | 91.9 | 91.0 | — | 20.0 | 8.0 | — |
| 9. ZnO/LAS acid = 1:2.0 | 91.6 | 91.3 | 90.8 | 20.5 | 6.0 | 2.0 |
| 10. ZnO/LAS acid = 1:2.04 | — | 91.0 | — | — | 4.0 | — |
| 11. ZnO/LAS acid = 1:2.1 | — | 90.3 | — | — | 4.0 | — |
| 12. ZnO/LAS acid = 1:2.5 | — | 88.8 | — | — | 11.5 | — |
| 13. Zn(O$_3$SCH$_2$CH$_2$OH)$_2$ | 92.2 | 93.4 | 93.8 | 7.5 | 4.0 | 1.5 |
| 14. Zn salt of C$_{14}$-C$_{16}$ α-olefin sulfonic acids | — | — | 91.8 | — | — | 4.5 |
| 15. Zn methane sulfonate | 92.3 | — | 93.5 | 9.0 | — | 1.0 |
| 16. Zn p-toluene sulfonate | 91.8 | — | 94.0 | 7.0 | — | 3.0 |
| 17. Zn(O$_3$SR)$_2$* | 93.3 | — | 93.1 | 26.0 | — | 1.0 |
| 18. Zn(O$_3$SR$^1$)$_2$** | 91.5 | — | 91.7 | 13.0 | — | 1.0 |

*mixed zinc salts of C$_{10-14}$ alkane-1-sulfonic acids
**mixed zinc salts of C$_{13-17}$ random paraffin sulfonic acids The data indicate that Zn salts of organic sulfonic acids either added as such or formed in situ provide a higher conversion of sodium isethionate into DEFI than the control (ZnO) in the same reaction time (i.e., 90 minutes). The data also indicate that the product color obtained by the use of the higher yielding catalytic system are undesirable, the yellowness index being greater than 6.0, when the higher yielding catalytic system is employed in the standard manner (Mode A). However, when the manner of addition of the catalytic system is changed to Mode B or C, the yellowness index surprisingly decreases to a significant degree. A product with a preferred yellowness index less than 3.0 is obtained by employing Mode C.

The data further indicate the regardless of whether mode B or C is utilized, in order to obtain a yellowness index less than 6.0 and to obtain optimum yields of the product, the molar ratio of ZnO/organic sulfonic acid should be kept about equal to or below the stoichiometric ratio (i.e. 1:2.0). However, it has been found that a significant corrosion of the stainless steel reaction vessel (e.g. stainless steel 316) occurs at or near said stoichiometric ratio. Since stainless steel is the material of choice for reaction vessels used in commercial operation, it is critical that the ratio of ZnO/organic sulfonic acid is maintained below said stoichiometric ratio, preferably at about or below 1:1.7 (e.g. 1:1.6; 1:1.5; 1:0.9 etc.) so that damage to the reaction vessel is minimized.

In order to determine corrosion, a test sample of a half-moon shaped stirrer blade made of stainless steel type 316 (the DEFI reactor material of construction) about 1.5 mm thick and 20 mm radius and approximately 12.4 cm² in surface area is used. Corrosiveness is measured by taking the weight of the 316 stainless steel blade before and after DEFI runs. After each run the blade is washed with water, rinsed with acetone and finally dried before weighing. The blade is re-polished with a fine Emery paper between different series of corrosion tests. Table 2 shows the results of such a corrosion study.

TABLE 2

CORROSION EFFECT OF CATALYST SYSTEM ON STAINLESS STEEL TYPE 316

| Catalyst | Molar Ratio | 1 | 2 | 3 | 4 | 5 | 6 | 7 | Avg. | Stainless Steel weight loss mg/25 cm²/run |
|---|---|---|---|---|---|---|---|---|---|---|
| A. Lauric Acid DEFI runs | | | | | | | | | | |
| 1 Control (ZnO) | — | 85.2 | 86.7 | 84.7 | 85.3 | 85.2 | — | — | 85.4 | 0.2 |
| 2 ZnO/LAS acid | 1:1.9 | 90.5 | 90.7 | 90.1 | 90.7 | 90.4 | 90.2 | 89.4 | 90.3 | 2.4 |
| 3 ZnO/LAS acid | 1:1.7 | 92.4 | 91.3 | 91.1 | — | — | — | — | 91.6 | 0 |
| 4 ZnO/LAS acid | 1:1.5 | 90.3 | 89.9 | 88.9 | — | — | — | — | 89.7 | 0 |
| 5 ZnO/LAS acid | 1:1.3 | 89.5 | 90.4 | 90.1 | — | — | — | — | 90.0 | 0 |
| 6 ZnO/LAS acid | 1:0.9 | 88.1 | 87.4 | 88.3 | — | — | — | — | 87.9 | 0 |
| 7 ZnO/LAS acid | 1:0.5 | 84.9 | 88.3 | 86.9 | — | — | — | — | 86.7 | 0 |
| B. Coconut DEFI runs | | | | | | | | | | |
| 1 ZnSO₄ | — | 89.4 | 87.9 | 88.4 | 88.7 | 89.3 | — | — | 88.7 | 0.6 |
| 2 ZnSO₄/LAS | 1:1.5 | 89.6 | 91.3 | 91.1 | 91.9 | 91.8 | — | — | 91.1 | 1.2 |
| 3 ZnO/LAS acid | 1:1.7 | 92.4 | 91.5 | 92.3 | 92.3 | 91.2 | — | — | 91.9 | 0.4 |

It is understood that the examples and embodiments described herein are for illustrative purposes only and that various modifications or changes in the light thereof will be suggested to persons skilled in the art and are to be included within the spirit and purview of this application and the scope of the appended claims.

What is claimed is:

1. A method of producing directly esterified fatty acyl isethionate consisting essentially of reacting a fatty acid with an alkali metal isethionate in the presence of a catalyst comprising a mixture of ZnO and an organic sulfonic acid wherein the molar ratio of ZnO to organic sulfonic acid is about 1:1.7 to about 1:0.5 and heating at about 200° C. to about 255° C. for sufficient time to produce the desired directly esterified fatty acyl isethionate.

2. A method according to claim 1 wherein said catalyst is a mixture of ZnO and a pre-prepared zinc salt of organic sulfonic acid.

3. A method according to claim 1 wherein said alkali metal isethionate is premixed with said catalyst and added to the fatty acid charge all at once.

4. A method according to claim 1 wherein said organic sulfonic acid is selected from the group consisting of isethionic acid, methane sulfonic acid; p-toluene sulfonic acid; linear $C_{10\text{-}15}$ alkylbenzene sulfonic acids; $C_{14}$-$C_{16}$ α-olefin sulfonic acid, $C_{10\text{-}14}$ alkane-1-sulfonic acids; $C_{13\text{-}17}$ random paraffin sulfonic acids and mixtures thereof.

5. A method according to claim 1, 2 or 3 wherein said directly esterified fatty acyl isethionate has a yellowness index equal to or less than about 6.0.

* * * * *